United States Patent [19]

Cattanach

[11] Patent Number: 5,013,297
[45] Date of Patent: May 7, 1991

[54] VAGINAL DOUCHE

[76] Inventor: John F. Cattanach, 140 Power Street, Hawthorn, Victoria 3122, Australia

[21] Appl. No.: 294,555

[22] Filed: Dec. 12, 1988

[30] Foreign Application Priority Data

Apr. 21, 1987 [AU] Australia ................... PI1507
Apr. 21, 1988 [WO] PCT Int'l
                    Appl. .......... PCT/AU88/00116

[51] Int. Cl.$^5$ ............................................ A61M 31/60
[52] U.S. Cl. ................................................... 604/55
[58] Field of Search .................. 604/27, 28, 36-42, 604/47, 54, 55

[56] References Cited

U.S. PATENT DOCUMENTS

| 471,647 | 3/1892 | Magoris | 604/39 |
| 900,182 | 10/1908 | Mayers | 604/39 |
| 1,591,410 | 7/1926 | Spang | 604/40 |
| 1,719,315 | 5/1926 | Strom | |
| 2,047,437 | 7/1932 | Sinkler | 128/232 |
| 2,478,802 | 9/1949 | Arnold | 604/41 |
| 2,552,469 | 5/1951 | Wahlbeck | 128/232 |
| 2,650,592 | 9/1953 | Borda | 128/227 |
| 3,581,743 | 7/1968 | Stein et al. | 128/232 |
| 3,690,319 | 9/1972 | Marco et al. | 604/106 |

FOREIGN PATENT DOCUMENTS

| 219449 | 2/1958 | Australia . |
| 3360184 | 9/1983 | Australia . |
| 8504106 | 9/1985 | Australia . |
| 551974 | 4/1923 | France . |
| 588425 | 5/1925 | France . |
| 642131 | 4/1928 | France . |

Primary Examiner—David J. Isabella

[57] ABSTRACT

A douching device (1) for administering a douche solution to a human female vagina. The device (1) includes a discharge member (2) having an elongate body (4) of generally thin walled tubular construction and composed at least substantially of a flexible material. The body (4) defines an elongate flow passage (5) having an inlet end (6) connectable to a container (3) having a supply of douche solution. The passage (5) also has an outlet end (7) at which there is an array of outlet openings (11) for discharging solution in a spray pattern. The device (1) can form part of a douching kit also including an applicator instrument (13) for inserting the discharge member (2) into the vagina. The instrument (13) is composed of stiff material and is elongate with leading and trailing end regions (14, 16). In use the discharge member (2) is positioned to lie in a collapsed condition along the instrument (11). Then the instrument (11) is inserted in an elongate direction into the vagina, the leading end region leading (14), so as to carry the discharge member (2) into the vagina until the outlet end (7) is located toward the cervix and the inlet end (6) remains external of the vagina. The instrument (11) is then withdrawn to leave the discharge member (2) in place.

16 Claims, 2 Drawing Sheets

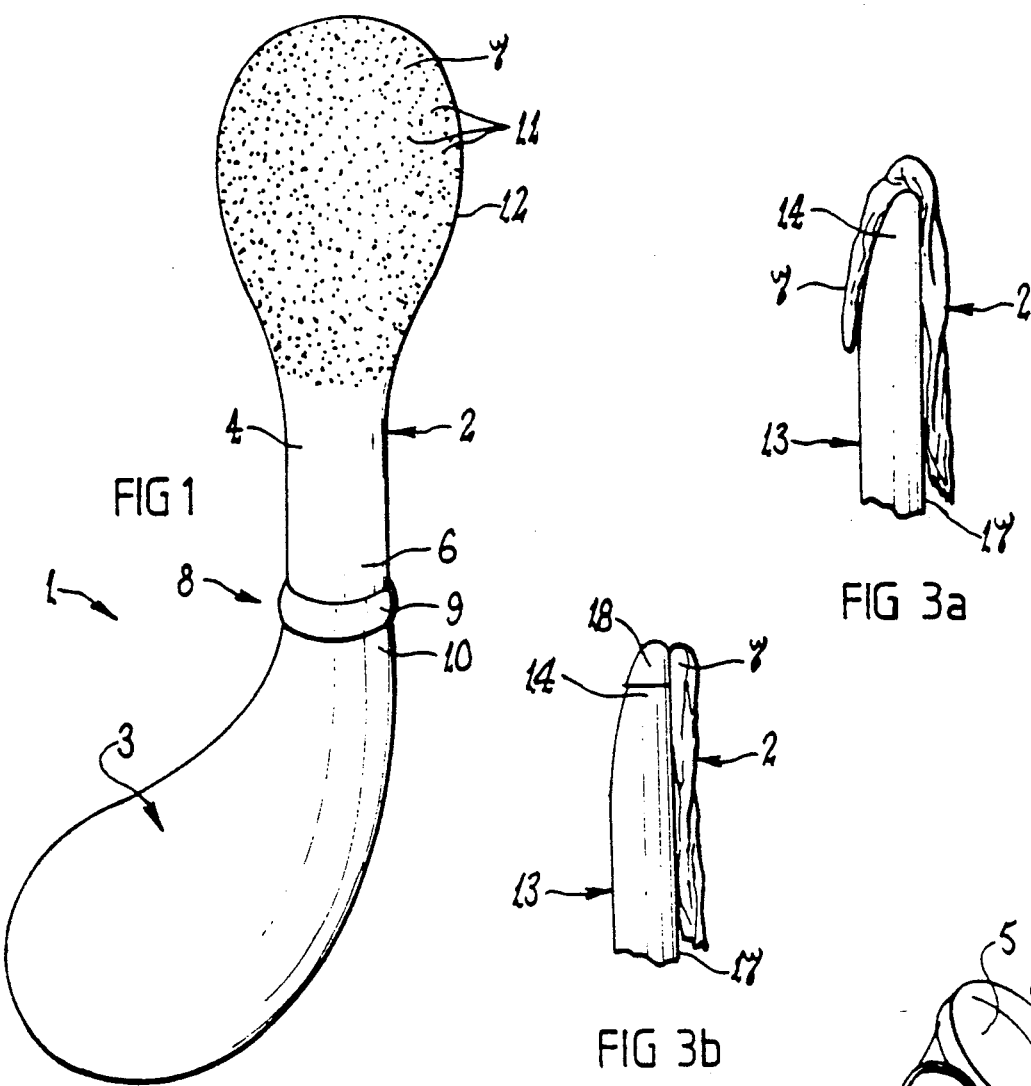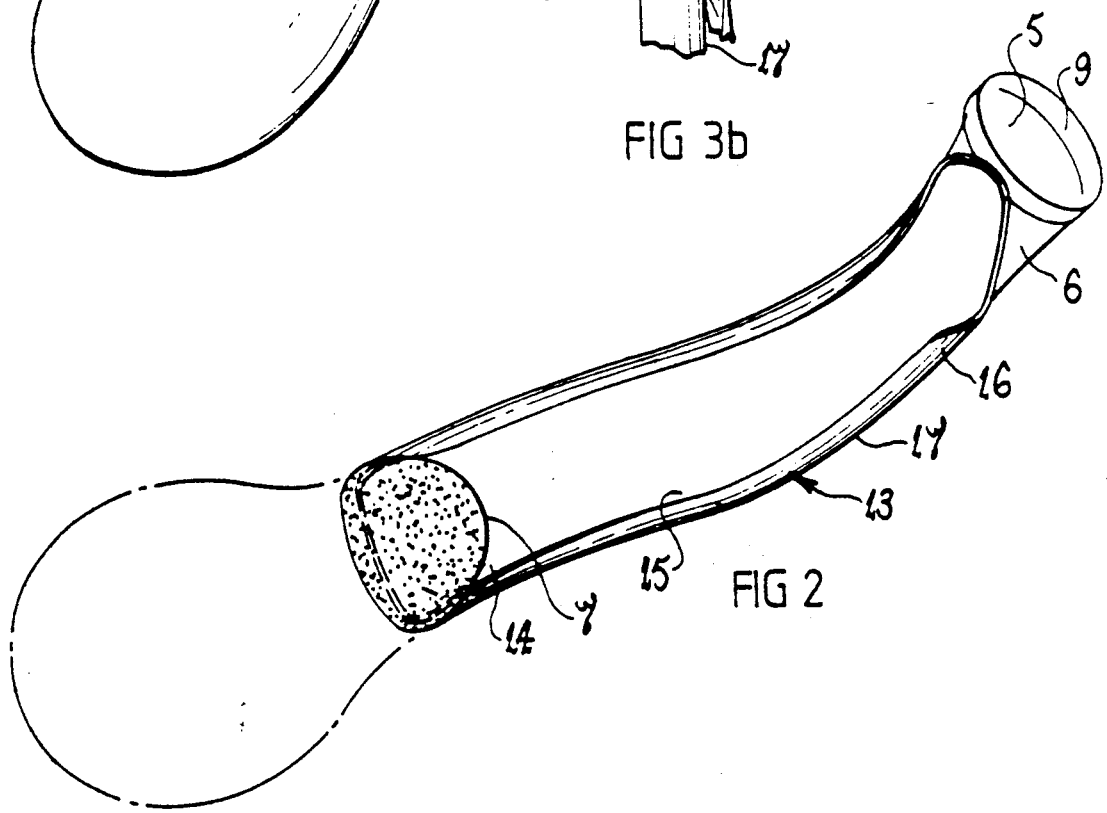

VAGINAL DOUCHE

BACKGROUND OF THE INVENTION

1. Field of the Invention

This invention relates generally to douching of the female human vagina, and in particular to a douching device and douching kit, as well as a douching method, for effectively administering a preventive douche solution to the vagina, especially to the vaginal lining at the inner end about the cervix. The device is applicable with douche solutions proposed to combat viruses of sexually transmitted diseases, including those causing Acquired Immune Deficiency Syndrome (AIDS). It will be convenient to hereinafter disclose the device and kit in relation to that exemplary application, although it is to be appreciated that the device is not limited to that application but may be used with other douche solutions including those used as a contraceptive against spermatoza.

2. Description of the Prior Art

Various douching devices have been developed for personal administration of a douche solution into the vagina. These devices are usually of a simple construction having a short stiff spout, sometimes curved along its length, for inserting along the vagina and a squeezable container for holding a quantity of douche solution and connectable to the spout. Manual squeezing of the container forces the solution to flow along the spout into the vagina. The terminal end of the spout is provided with one or more holes so that the solution is generally spray discharged.

It has been found that in general these devices provide only a limited douching effect, then only if expertly handled. In that regard, often the solution is administered only toward the outer end of the vagina so that the solution does not reach the inner end about the cervix where required. This is caused by only partially inserting the spout, sometimes the result of poor or uneducated use of the device and at other times the result of difficulties in properly inserting the spout. Even when completely inserted the terminal end holes are usually so limited in number and/or placement that the solution discharge is eratic and solution application through the vagina uneven.

Moreover, these devices can be uncomfortable if not painful to use. In that regard, the spout is made of relatively stiff material so as to ensure that it does not collapse and prevent insertion. However, upon insertion the spout does not always smoothly follow the curve of the vaginal tract but rather rubs against the vaginal lining tissues, uncomfortably distorting the vagina.

The large physical size of previous douching devices is such that it is often not convenient to carry at all those times when a need for its use might be anticipated or arise. That in turn may somewhat restrict the actual use of the device and possibly limit the preventive potential of douche solutions.

SUMMARY OF THE INVENTION

It is an object of the present invention to provide a douching device that alleviates these disadvantages. It is another object of the invention to provide relatively small and simple device that can be easily used to effectively administer a douche solution to the vagina. A further object is to provide a simple discharge member forming part of a douching device. Yet another object of the invention is the provision of a compact and easy to use a douching kit incorporating the above device and an applicator instrument.

With those objects in mind, the present invention provides in one aspect a discharge member of a douching device insertable into a female vagina for administering a douche solution thereto, the discharge member including an elongate body of generally thin walled tubular construction and composed at least substantially of a flexible material, the body defining an elongate flow passage extending therealong having an inlet end at which the body is connectable to a supply of douche solution and a spaced apart outlet end at which the body has an array of outlet openings through which solution is discharged in a spray pattern.

In another aspect, the present invention provides a douching device for administering a douche solution to a human female vagina, including: the above discharge member; and, a container for holding a quantity of douche solution and connectable to the inlet end of the discharge member body for supplying douche solution thereto.

A further aspect of the present invention provides a douching kit for administering a douche solution to a human female vagina, including: the above douching device; and, an applicator instrument for inserting the discharge member of the douching device into the vagina, the instrument being composed of stiff material and being elongate with opposite leading and trailing end regions, the discharge member being positionable so as to lie in a collapsed condition along the instrument with the outlet end adjacent the leading end region and the inlet end adjacent the trailing end region, and with the discharge member so positioned the instrument being insertable in an elongate direction into the vagina, the leading end region leading, so as to carry the discharge member into the vagina therewith until the outlet end is located toward the cervix and the inlet end remains external of the vagina.

Preferably, the discharge member body is shaped adjacent the outlet end so that, during use, the body adopts a rounded configuration adjacent the outlet end. As a result, a curved outer wall surface is formed at the outlet end and the outlet openings are arranged over the outer wall surface. The discharge member body may be shaped adjacent the outlet end so as to adopt an enlarged bulbous configuration at the outlet end during use. Moreover, the outlet openings may be arranged over this bulbous configured outlet end so as to spray discharge douche solution over a substantially spherical pattern.

Preferably, connection means are provided at the inlet end of the discharge member body for releasable connection of the member to the supply of douche solution. That connection means may include a connection device secured to the discharge member body so as to surround the inlet end, the connection device being releasably snap-lock connectable to a further, cooperating connection device provided by the container source of douche solution supply.

In another aspect of the present invention, there is provided a method of administering a douche solution to a human female vagina using the above douching kit. That method includes the steps of: positioning the discharge member so as to lie in a collapsed condition along the instrument with the outlet end adjacent the leading end region and the inlet end adjacent the trailing end region; inserting the instrument and discharge member lying therealong in an elongate direction into the vagina, the leading end region leading, so as to carry the discharge member into the vagina therewith until the outlet end is located toward the cervix and the inlet end remains external of the vagina; withdrawing the instrument from the vagina to leave the discharge member in the vagina; delivering douche solution from the container to the inlet end of the discharge member body for flow along the flow passage and discharge in a spray pattern from the outlet openings into the vagina; and, withdrawing the discharge member from the vagina.

The discharge member is preferably positioned so that the body lies along an elongate outer surface of the instrument with the outlet end protruding from the leading end region and the inlet end trails from the trailing end region. During positioning of the discharge member the outlet end may be folded back over the leading end region to retain the discharge member on the instrument during insertion into the vagina. Alternatively, the discharge member body may be provided with a pocket adjacent the outlet end and the leading end region of the instrument may be received in the pocket so as to retain the discharge member on the instrument.

This method preferably includes the further step of connecting the inlet end of the discharge member body to the container after positioning of the discharge member in the vagina.

In this method, the douche solution may be discharged from the outlet openings whilst the discharge member is slowly withdrawn from the vagina.

The following description refers to a preferred embodiment of the douching device and kit of the present invention, as well as a douching method utilizing the douching kit. To facilitate an understanding of the invention, reference is made in the description to the accompanying drawings where the douching device and kit are illustrated in that preferred embodiment. It is to be understood that the invention is not limited to the preferred embodiment as hereinafter described and as illustrated in the drawings.

BRIEF DESCRIPTION OF THE DRAWING FIGURES

FIG. 1 is a perspective view of a preferred embodiment of the douching device of the present invention, with the discharge member being inflated as will generally occur in use;

FIG. 2 is a perspective view of the discharge member from the device of FIG. 1 when supported by an applicator instrument of the douching kit ready for insertion in a vagina, and with the discharge end portion of the discharge member being chain dotted as in a use configuration.

FIG. 3a is a side view of the discharge member and applicator instrument of FIG. 2 adjacent the discharge end portion;

FIG. 3b is a side view of the discharge member and application instrument similar to FIG. 3a, but showing a modified discharge member;

DETAILED DESCRIPTION OF THE PREFERRED EMBODIMENT

Figure 4:
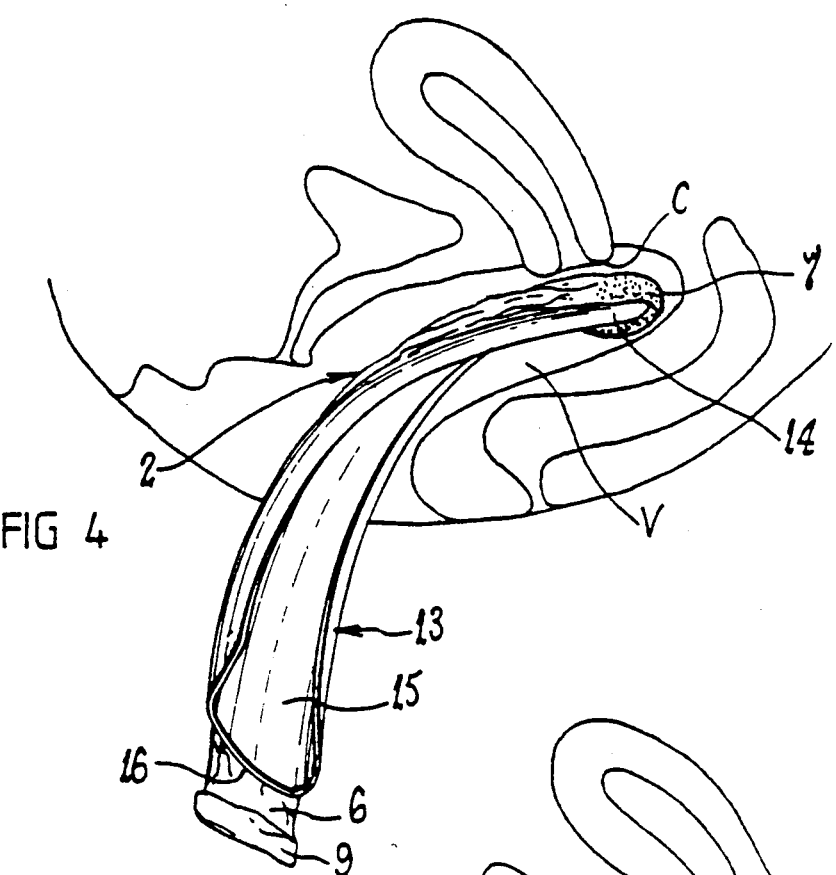
FIG. 4 is a diagrammatic side view of the female human pelvic organs showing the location of the discharge member and applicator instrument of FIG. 2 inserted into the vagina but prior to douching; and, FIG. 5 is a side view similar to FIG. 4 but showing the douching device in use and the applicator instrument removed.

Referring initially to FIG. 1 there is generally illustrated douching device 1 including discharge member 2 connected to douching solution container 3.

Discharge member 2 has generally elongate tubular body 4 providing elongate flow passage 5 having spaced apart inlet end 6 and outlet end 7. Undistorted, discharge member 2, and in particular body 4 may be generally straight and of an annular cross-sectional shape, although it should be appreciated that other configurations may be equally suitable. In this preferred embodiment, body 4 is at least substantially smooth walled.

Discharge member body 4 is of an integral one piece construction. Member body 4 may be constructed by molding from a suitable material. That molding produces a thin walled body of flexible or pliant construction, permitting ready distortion of member 2 thereby facilitating insertion into the vagina. Discharge member body 4 may be composed of any material toxically inert in the exemplary application, including selected plastics materials and synthetic rubber materials.

Inlet end 6 of discharge member body 4 is constructed to facilitate connection to container 3. Container 3 may be of a hand held, squeezable construction for delivering solution to discharge member 2, although it should be appreciated that other constructions may be equally suitable.

Connection between inlet end 6 and container 3 is preferably provided by easily releasable connection means 8. In that regard, member 2 may be disconnected from container 3 for initial insertion into the vagina whereupon container 3 is connected thereto for solution delivery. Moreover, that connection preferably provides a liquid seal and is sufficiently secure to withstand the solution pressures developed during delivery from the container 3 into the vagina.

Within these constrains container 3 may be of any suitable arrangement. In one form (as illustrated) discharge member 2 may include rim 9 at inlet end 6 shaped and sized to receive outlet snout 10 of container 3. Rim 9 may simply expand about and firmly grip snout 10, or a fastening clip, collar, or ferrule or other retained element (not illustrated) may be provided to positively secure rim 9 thereto. In another form (not illustrated) rim 9 may be constructed of relatively stiff material (compared to body 4) and connect to container snout 10 through interengaging coupling elements of connection devices such as through screwthreads or through a snap-lock arrangement.

Outlet end 7 of discharge member body 4 has outlet openings 11 arranged to spray douche solution delivered through flow passage 5 over a substantially spherical pattern. As a result, the solution is discharged axially of outlet end 7 along the vagina as well as radially of outlet end 7 laterally of the vagina. In this way, when outlet end 7 is positioned toward the inner end of the vagina adjacent the cervix the solution is sprayed in a pattern that at least substantially douches the vaginal linings at the inner end.

At least during use of discharge member 2, outlet end 7 is of somewhat rounded configuration so as to form curved outer wall surface 12. Outlet openings 11 are arranged over that wall surface 12. The flexible nature of member body 4 may mean that outlet end 7 is flattened, squashed, or otherwise distorted during insertion into the vagina and subsequently takes on the rounded configuration under pressure of solution delivered thereto.

In this preferred embodiment, outlet end 7 is of a bulbous shape when discharging solution. Outlet end 7 maybe laterally enlarged compared to remainder of body 4. Moreover, that end 7 may comprise a single large bulge (as illustrated) or two or more smaller bulges (not illustrated) spaced about end 7 and extending in different outward directions from the longitudinal extent of discharge member 2.

Generally, the flexible nature of outlet end 7 will mean that end 7 is collapsed prior to and during vaginal insertion, and subsequently expands into the bulbous shape under pressure of douche solution delivered thereto. In the collapsed condition, end 7 may be specifically and deliberately pleated or folded. This may minimise the end size to facilitate insertion, and also assist achieving rapid and complete expansion into the bulbous shape.

Any suitable number and array of outlet openings 11 may be provided at outlet end 7, depending on the required spray pattern. Importantly, however, the pattern will maximise the likelihood of sprayed solution contacting the entire vaginal linings.

Because of the pliable, almost limp, nature of discharge member body 4 applicator instrument 13, as illustrated (in FIGS. 2 and 3) is used to facilitate proper and complete insertion. Whilst a number of instruments may be suitable, one particularly appropriate instrument 13 (as illustrated) is disclosed in U.S. Pat. No. 4,848,363 corresponding to Australian Patent Application 62709/86. The disclosure of that instrument is incorporated herein by reference. It should be appreciated, however, that the instrument is not limited to that one disclosed in the referenced patent application.

An advantage of the instrument of application 62709/86 is the ability and ease with which it can be inserted into the vagina until the leading end region 14 reaches the cervix and inner wall of the vagina. Thus, if discharge member 2 is supported by instrument 13 with outlet end 7 adjacent leading end region 14, then upon instrument insertion outlet end 7 will be located at the inner end of the vagina for douching of the linings thereof. Discharge member 2 is supported so that outlet end 7 protrudes forwardly of leading end region 14, at least during solution spraying when end 7 expands into its bulbous shape.

In one preferred embodiment (not illustrated), discharge member 2 is supported by loading into open sided passage 15 extending along instrument 13. Outlet end 7 protrudes from leading end region 14 whilst inlet end 6 trails rearwardly of trailing end region 16.

In another preferred embodiment (as illustrated in FIGS. 3a and 3b,) discharge member 2 is carried on outer surface 17 of instrument 13 by holding it taut between leading and trailing end regions 14, 16. That may be achieved by folding outlet end 7 back over end region 14 (as illustrated in FIG. 3a), or providing discharge member 2 with a pocket 18 (as illustrated in FIG. 3b)) at or adjacent outlet end 7 into which leading end region 14 can be received. Discharge member body 4 can then be drawn along instrument outer surface 17 until inlet end 6 is manually held at trailing end region 16 of instrument 13. Held in this position instrument 13 and discharge member 2 can be inserted together into the vagina.

To position discharge member 2 within a vagina, member 2 is initially loaded into or onto applicator instrument 13 as illustrated in FIG. 2 (full line). When correctly loaded, outlet end 7 will be located at and may protrude slightly forwardly of the leading end region 14. At this stage, douche solution container 3 need not be connected to discharge member Manually holding instrument 13 and supported discharge member 2, instrument 13 is then gently plunged into vagina V (as illustrated in FIG. 4) with leading end region 14 moving progressively therealong toward cervix C. That movement of instrument 13 is as described in the referenced patent application 62709/86 and continues until leading end region 14 reaches cervix C. This movement causes discharge member 2 to move along vagina V until outlet end 7 is located at the inner end adjacent cervix C.

Figure 5:
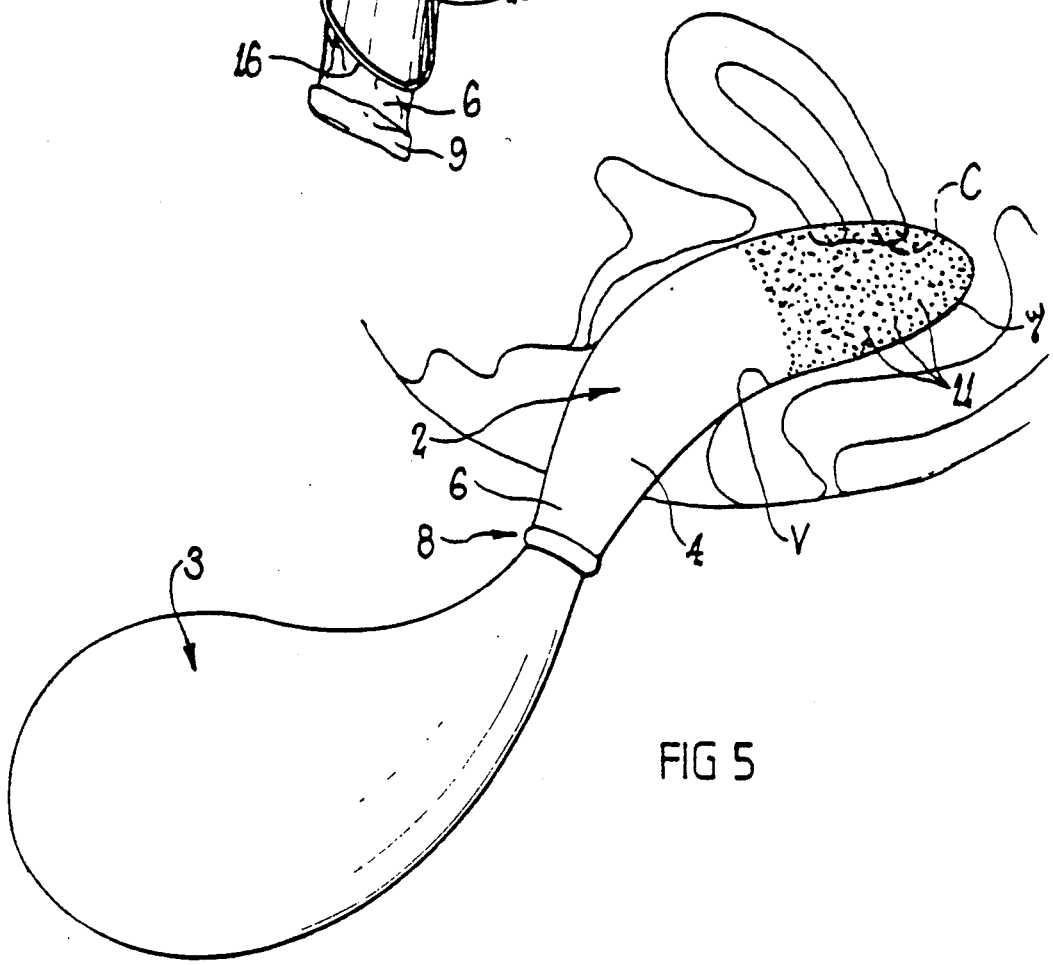

Container 3 with douche solution is then connected to inlet end 6. Solution is then caused to flow along passage 5 and sprayed through outlet openings 11. That solution flow causes outlet end 7 to expand into its bulbous shape (as illustrated in FIG. 5) so that outlet openings 11 are directed throughout the inner end of vagina V. Instrument 13 may be retained within the vagina V or removed therefrom for douching (as illustrated). As douching proceeds, discharge member 2 is progressively withdrawn so as to ensure that the solution is sprayed entirely along the vaginal tract.

Preferably douching will be undertaken whilst the person is reclined. Moreover, following douching the person should remain on her back for several minutes to maximise contact of the solution with the vaginal linings.

The discharge member according to the present invention maximises administration of douche solutions throughout the vagina including the inner end linings adjacent the cervix. That is achieved to some extent by the ease with which the member is inserted into the vagina. Moreover, a particularly effective spray discharge of the douche solution can be achieved by the discharge member once inserted. As a result vaginal douching may be more effective utilising the discharge member and douching device of the present invention when compared to previous devices.

The douching device and kit of the present invention can be relatively compact in size and therefore readily carried in anticipation of use. This may therefore increase the potential use of douching devices and douche solutions.

Finally, it is to be appreciated that various modifications and/or alterations may be made to the douching device and discharge member thereof without departing from the ambit of the present invention as defined in the claims appended hereto.

I claim:

1. A douching device for administering douche solution to a human female vagina, comprising:
   a discharge member insertable into a female vagina for administering a douche solution thereto, said discharge member including
   an elongate body of generally thin walled tubular construction and composed at least substantially of a flexible material, the body including
   means defining an elongate flow passage extending therealong having an inlet end at which the body is connectable to a supply of douche solution, and
   means defining a spaced apart outlet end having an array of outlet openings through which solution is discharged in a spray pattern as claimed in any preceding claim;

a container for holding a quantity of douche solution and connectable to the inlet end of the discharge member body for supplying douche solution thereto; and an applicator instrument separate from and exterior to the discharge member for inserting the discharge member into the vagina, the instrument being composed of stiff material and being elongate with opposite leading and trailing end regions, the discharge member being positionable so as to lie in a collapsed condition along the instrument with the outlet end adjacent the leading end region and the inlet end adjacent the trailing end region, and with the discharge member so positioned, the instrument being insertable in an elongate direction into the vagina, the leading end region leading, so as to carry the discharge member into the vagina therewith until the outlet end is located toward the cervix and the inlet end remains external of the vagina, the applicator instrument thereafter being withdrawable from the vagina to leave the discharge member extending along the vagina.

2. The douching device as claimed in claim 1, wherein the discharge member body is shaped adjacent the outlet end so that, during use, the body adopts a rounded configuration adjacent the outlet end thereby providing a curved outer wall surface, the outlet openings being arranged over the outer wall surface.

3. The discharge member as claimed in claim 2, wherein the discharge member body is shaped adjacent the outlet end so as to adopt an enlarged bulbous configuration at the outlet end during use.

4. The douching device as claimed in claim 1, wherein the outlet openings are arranged so as to spray discharge douch solution over a substantially spherical pattern.

5. The douching device as claimed in claim 1, wherein the discharge member body includes structure defining a pocket adjacent the outlet end for receiving an applicator instrument facilitating insertion of the discharge member into the vagina.

6. The douching device as claimed in claim 1, and further including connection means at the inlet end of the discharge member body for releasable connection of the member to the supply of douche solution.

7. The discharge member as claimed in claim 6, wherein the connection means includes a connection device secured to the discharge member body so as to surround the inlet end, the connection device being releasably snap-lock connectable to a further, cooperating connection device provided by a source of douche solution supply.

8. The douching device as claimed in claim 1, wherein the instrument has an elongate outer surface extending at least substantially entirely therealong, and along which the discharge member is positioned to lie so that the outlet end protrudes from the leading end region and the inlet end trails from the trailing end region.

9. The method of administering a douche solution to a human female vagina including the steps of:

providing a discharge member having an elongated body of generally thin-walled tubular construction and composed at least substantially of a flexible material, the body including means defining an elongated flow passage extending therealong having an inlet end at which the body is connectable to a supply of douche solution, and means defining a spaced-apart outlet end having an array of outlet openings through which solution is discharged in a spray pattern;

providing an applicator instrument separate from and exterior to the discharge member, the instrument being composed of stiff material and being elongate with opposite leading and trailing end regions;

positioning the discharge member so as to lie in a collapsed condition along the instrument with the outlet end adjacent the leading end region and the inlet end adjacent the trailing end regions;

inserting the instrument and discharge member lying therealong in an elongate direction into the vagina, the leading end region leading, so as to carry the discharge member into the vagina therewith until the outlet end is located toward the cervix and the inlet end remains external of the vagina;

withdrawing the instrument from the vagina to leave the discharge member in the vagina;

providing a container of douche solution;

delivering douche solution from the container to the inlet end of the discharge member body for flow along the flow passage and discharge in a spray pattern from the outlet openings into the vagina; and withdrawing the discharge member from the vagina.

10. The method as claimed in claim 9, said positioning step including the step of positioning the discharge member so that the body lies along an elongate outer surface of the instrument with the outlet end protruding from the leading end region and the inlet end trails from the trailing end region.

11. The method as claimed in claim 10, further including the step of folding back the outlet end over the leading end region to retain the discharge member on the instrument during insertion into the vagina during positioning of the discharge member on the instrument.

12. The method as claimed in claim 10, further including the steps of providing the discharge member body with structure defining a pocket adjacent the outlet end, and, receiving the leading end region of the instrument in the pocket so as to retain in the discharge member on the instrument during insertion into the vagina during positioning of the member to lie along the instrument.

13. A method as claimed in claim 9, including the further step of connecting the inlet end of the discharge member body to the container after positioning of the discharge member in the vagina.

14. A method as claimed in claim 13, including the step of discharging the douche solution from the outlet openings while the discharge member is slowly withdrawn from the vagina.

15. The method of administering a douche solution to a human female vagina including the steps of:

providing a discharge member having an elongated body of generally thin-walled tubular construction and composed at least substantially of a flexible material, the body including means defining an elongated flow passage extending therealong having an inlet end at which the body is connectable to a supply of douche solution, and means defining a spaced-apart outlet end having an array of outlet openings through which solution is discharged in a spray pattern;
providing an applicator instrument separate from and exterior to the discharge member, the instrument being composed of still material and being elongate with opposite leading and trailing end regions;
positioning the discharge member so as to lie in a collapsed condition along the instrument with the outlet end adjacent the leading end region and the inlet end adjacent the trailing end regions;
inserting the instrument and discharge member lying therealong in an elongate direction into the vagina, the leading end region leading, so as to carry the discharge member into the vagina therewith until the outlet end is located toward the cervix and the inlet end remains external of the vagina;
withdrawing the instrument from the vagina to leave the discharge member in the vagina;
providing a container of douche solution;
delivering douche solution from the container to the inlet end of the discharge member body for flow along the flow passage and discharge in a spay pattern from the outlet openings into the vagina; and
withdrawing the discharge member from the vagina.
said positioning step including the step of positioning the discharge member so that the body lies along an elongate outer surface of the instrument with the outlet end protruding from the leading end region and the inlet end trails from the trailing end region; and
said method further including the steps of folding back the outlet end over the leading end region to retain the discharge member on the instrument during insertion into the vagina during positioning of the discharge member on the instrument.

16. The method of administering a douche solution to a human female vagina including the steps of:
providing a discharge member having an elongated body of generally thin-walled tubular construction and composed at least substantially of a flexible material, the body including
means defining an elongated flow passage extending therealong having an inlet end at which the body is connectable to a supply of douche solution, and
means defining a spaced-apart outlet end having an array of outlet openings through which solution is discharged in a spray pattern;
providing an applicator instrument separate from and exterior to the discharge member, the instrument being composed of stiff material and being elongate with opposite leading and trailing end regions;
positioning the discharge member so as to lie in a collapsed condition along the instrument with the outlet end adjacent the leading end region and the inlet end adjacent the trailing end regions;
inserting the instrument and discharge member lying therealong in an elongate direction into the vagina, the leading end region leading, so as to carry the discharge member into the vagina therewith until the outlet end is located toward the cervix and the inlet end remains external of the vagina;
withdrawing the instrument from the vagina to leave the discharge member in the vagina;
providing a container of douche solution;
delivering douche solution from the container to the inlet end of the discharge member body for flow along the flow passage and discharge in a spray pattern from the outlet openings into the vagina;
withdrawing the discharge member from the vagina,
said positioning step including the step of positioning the discharge member so that the body lies along an elongate outer surface of the instrument with the outlet end protruding from the leading end region and the inlet end trails from the trailing end region; and
said method further including the steps of providing the discharge member body with structure defining a pocket adjacent the outlet end, and, receiving the leading end region of the instrument in the pocket so as to retain in the discharge member on the instrument during insertion into the vagina during positioning of the member to lie along the instrument.

* * * * *